United States Patent [19]

Evers et al.

[11] Patent Number: 5,141,955

[45] Date of Patent: Aug. 25, 1992

[54] ANTI-INFLAMMATORY BENZYLSELENOBENZAMIDES MADE FROM ANILINES AND BENZYLAMINES

[75] Inventors: Michel Evers, Liege, Belgium; Hartmut Fischer, Cologne, Fed. Rep. of Germany; Jürgen Biedermann, Pulheim, Fed. Rep. of Germany; Rolf Terlinden, Cologne, Fed. Rep. of Germany; Sigurd Leyck, Pulheim, Fed. Rep. of Germany

[73] Assignee: A. Nattermann & Cie. GmbH, Cologne, Fed. Rep. of Germany

[21] Appl. No.: 611,272

[22] Filed: Nov. 8, 1990

[30] Foreign Application Priority Data

Nov. 8, 1989 [DE] Fed. Rep. of Germany ....... 3937169

[51] Int. Cl.$^5$ ............................................. A61K 31/095
[52] U.S. Cl. .................................... 514/466; 514/522; 514/617; 548/237; 549/439; 558/415; 562/899
[58] Field of Search ............... 562/899; 514/617, 466, 514/522; 549/439; 558/415

[56] References Cited

U.S. PATENT DOCUMENTS

| | | | |
|---|---|---|---|
| 3,321,021 | 11/1965 | Hickner | 548/229 |
| 3,947,465 | 3/1976 | Palomo-Coll | 548/229 |
| 4,418,069 | 11/1983 | Welter et al. | 548/121 |
| 4,588,432 | 5/1986 | Hillemann | 562/899 |
| 4,711,961 | 12/1987 | Welter | 548/121 |
| 4,730,053 | 3/1988 | Dereu et al. | 514/522 |
| 4,774,252 | 9/1988 | Welter | 548/121 |
| 4,873,350 | 10/1989 | Welter et al. | 562/899 |
| 4,942,178 | 7/1990 | Toyoda | 514/617 |
| 5,008,394 | 4/1991 | Günther et al. | 548/121 |

OTHER PUBLICATIONS

Burger, Medicinal Chemistry, 2d Ed., Interscience, N.Y., 1960, p. 42.
Advances in Inflammation Research, vol. 12, pp. 257, 262 (Raven Press, New York 1988).
John et al., Chem. Res. Toxicol. vol. 3, pp. 199-203 (1990).

Primary Examiner—Donald G. Daus
Attorney, Agent, or Firm—Herbert Dubno

[57] ABSTRACT

Anti-inflammatory benzylselanobenzamides made from anilines and benzylamines have the formula I

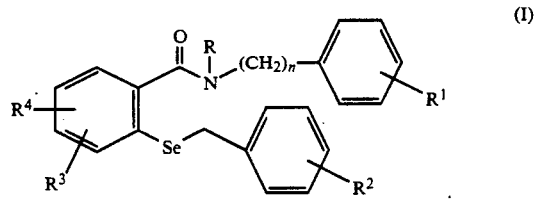

(I)

are disclosed wherein

R is hydrogen, methyl or ethyl;

$R^1$ and $R^2$ are the same or different and, taken separately, are hydrogen, fluorine, chlorine, bromine, $C_1$ to $C_4$ alkyl, $C_1$ to $C_4$ alkoxy, hydroxy, cyano, amino, dimethylamino or nitro; and $R^3$ and $R^4$ are the same or different and, taken separately, are hydrogen, fluorine, chlorine, bromine, $C_1$ to $C_4$ alkyl, $C_1$ to $C_4$ alkoxy, hydroxy, cyano, or nitro and, taken together, represent methylenedioxy; and n is 0.1 or 2.

5 Claims, No Drawings

ANTI-INFLAMMATORY BENZYLSELENOBENZAMIDES MADE FROM ANILINES AND BENZYLAMINES

FIELD OF THE INVENTION

The invention relates to novel benzylselenobenzamides, methods and intermediates for their preparation and pharmaceutical products containing these compounds.

DESCRIPTION OF THE INVENTION

The compounds to which this invention relates correspond to the formula I

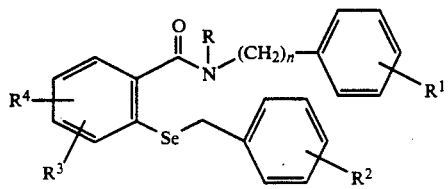

wherein
R is hydrogen, methyl or ethyl and
$R^1$, $R^2$ are the same or different and, taken separately, represent hydrogen, fluorine, chlorine, bromine, $C_{1-4}$-alkyl, $C_{1-4}$-alkoxy, hydroxy, cyano, amino, dimethylamino or nitro and
$R^3$, $R^4$ are the same or different and, taken separately, represent hydrogen, fluorine, chlorine, bromine, $C_{1-4}$-alkyl, $C_{1-4}$-alkoxy, hydroxy, cyano or nitro or, taken together, represent methylenedioxy and
n is zero, 1 or 2.

Benzylselenobenzamides of formula I are preferred where n equals zero and R, $R^2$, $R^3$ and $R^4$ represent hydrogen, while $R^1$ represents hydrogen, fluorine, chlorine, bromine, methyl, methoxy, hydroxy, cyano or nitro.

Another preferred group of benzylselenobenzamides of formula I is that where n equals zero and R, $R^1$, $R^3$ and $R^4$ represent hydrogen, while $R^2$ represents hydrogen, fluorine, chlorine, bromine, methyl, methoxy, hydroxy, cyano or nitro.

Also preferred are benzylselenobenzamides of formula I where n equals zero and R and $R^2$ represent hydrogen while $R^1$, $R^3$ and $R^4$ can be the same or different and, taken separately, represent hydrogen, fluorine, chlorine, bromine, methyl, methoxy, hydroxy, cyano, nitro, amino, dimethylamino or $R^3$ and $R^4$, taken together, represent methylenedioxy.

Examples of compounds to which the invention relates are:
N-(4-Methylphenyl)-2-benzylselenobenzamide
N-(4-Methoxyphenyl)-2-benzylselenobenzamide
N-(4-Fluorophenyl)-2-benzylselenobenzamide
N-(4-N',N'-Dimethylaminophenyl)-2-benzylselenobenzamide
N-(4-Hydroxyphenyl)-2-benzylselenobenzamide
N-(4-Chlorophenyl)-2-benzylselenobenzamide
N-(4-Cyanophenyl)-2-benzylselenobenzamide
N-(4-Nitrophenyl)-2-benzylselenobenzamide
N-Ethyl-N-(4-fluorophenyl)-2-benzylselenobenzamide
R(+)-N-(1-Phenylethyl)-2-benzylselenobenzamide
S(−)-N-(1-Phenylethyl)-2-benzylselenobenzamide
2-Benzylselenobenzanilide
N-Phenyl-2-(4-methylbenzylseleno)benzamide
N-Phenyl-2-(4-methoxybenzylseleno)benzamide
N-Phenyl-2-(4-bromobenzylseleno)benzamide
N-Phenyl-2-(4-cyanobenzylseleno)benzamide
N-Phenyl-2-(4-nitrobenzylseleno)benzamide
N-Phenyl-2-(4-fluorobenzylseleno)benzamide
N-Phenyl-2-(4-chlorobenzylseleno)benzamide
N-Phenyl-2-(3-chlorobenzylseleno)benzamide
2-Benzylseleno-3-methoxybenzanilide
2-Benzylseleno-3,4-methylenedioxybenzanilide
2-Benzylseleno-3-fluorobenzanilide
N-Ethyl-N-(4-fluorophenyl)-2-benzylseleno-3-fluorobenzamide
N-Benzyl-2-benzylseleno-3-fluorobenzamide
N-Methyl-N-phenyl-2-benzylseleno-3-methoxybenzamide and 2-Benzylseleno-3-chlorobenzanilide, The compounds to which the invention relates can be obtained from the active, isolable intermediates according to formula II or III.

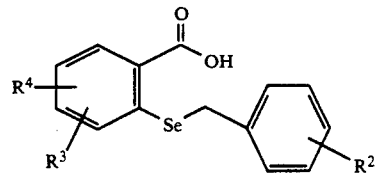

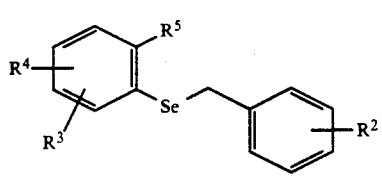

$R^5$ represents 1,3-oxazoline or 4,4-dimethyl-1,3-oxazoline.

The benzylselenobenzoic acids used as starting materials are prepared according to examples 1 to 13.

In general for this purpose a diselenosalicylic acid in aqueous solution is made alkaline with sodium hydroxide and treated with sodium carbonate and sodium dithionite, the reaction mixture treated with benzyl bromide and then neutralized with hydrochloric acid to yield the final product.

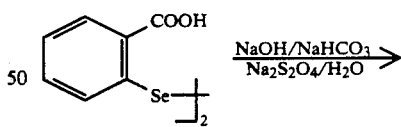

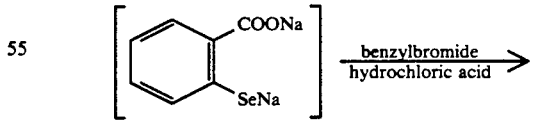

The following compounds, for example, are suitable for the synthesis of products of formula I:
2-(4-Methylbenzylseleno)benzoic acid
2-(4Methoxybenzylseleno)benzoic acid 2-(4-Bromobenzylseleno)benzoic acid 2-(4-Cyanobenzylseleno)benzoic acid 2-(4-Fluorobenzylseleno)benzoic acid 2-(4-Nitrobenzylseleno)benzoic acid 2-(3-Chlorobenzylseleno)benzoic acid 2-(4-Chlorobenzylseleno)benzoic acid 2-Benzylseleno-3-methoxybenzoic acid 2-Benzylseleno-3,4′-methilenedioxybenzoic acid 2-Benzylseleno-3-fluorobenzoic acid The benzylselenobenzoic acids are employed as active, isolable intermediates for the preparation of the benzylselenobenzamides according to formula I, whereby benzylselenobenzoic acids according to formula II, in a chlorinated hydrocarbon, are reacted with bis(2-oxo-3-oxazolidinyl)phosphoryl chloride and aniline and the resulting product is isolated from the reaction mixture.

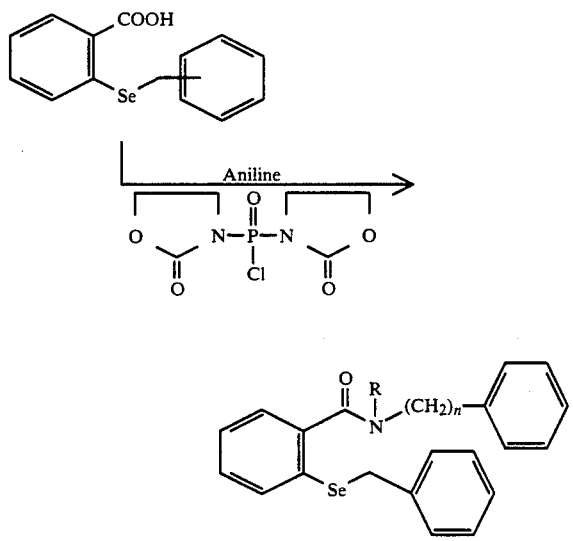

However, the compounds to which the invention relates can also be prepared by reacting an oxazoline compound of general formula V

where $R^3$ and $R^4$ have the meanings assigned in formula II in tetrahydrofuran with dibenzyl diselenide—with the addition of n-butyllithium in n-hexane—and isolating the product from the reaction mixture:

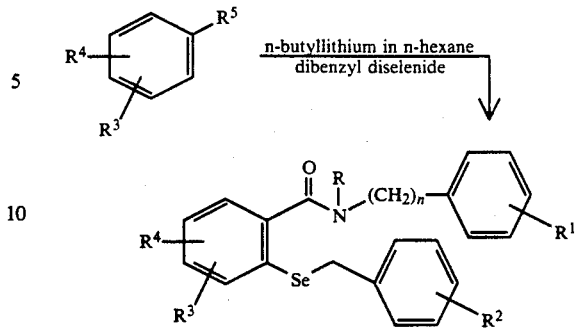

Suitable oxazoline compounds include, for example:

4,4-Dimethyl-2-(3,4-methylenedioxy)phenyl-1,3-oxazoline 4,4-Dimethyl-2-(3-methoxy)phenyl-1,3-oxazoline 4,4-Dimethyl-2-(3-fluoro)phenyl-1,3-oxazoline 4,4-Dimethyl-2-(3-chloro)phenyl-1,3-oxazoline as described by, for instance, A. I. Meyers, W. B. Avila, J. Org. Chem. 46 (1981), 3881–3886.

This invention also relates to pharmaceutical products containing compounds according to formula I as active ingredients. Pharmaceutical products to which the invention relates are enteral as well as oral, rectal or parenteral dosage forms which contain the pharmaceutically active ingredient either alone or together with a usual, pharmaceutically employed excipient. The pharmaceutical preparations of the active ingredient should preferably take the form of individual doses, which are adapted to the desired method of administration, such as, for example, tablets, dragées, capsules, suppositories, granules, solutions, emulsions or suspensions. The dosage of substance usually lies between 10 and 100 mg/day preferably between 30 and 300 mg/day and can be administered in one dose or distributed over several doses, preferably over two or three doses daily. The composition has excellent inflammation-inhibiting characteristics. The preparation of the substances to which the invention relates will be elucidated in more detail in the examples that follow.

The melting points quoted were determined using a Büchi 510 melting point determination apparatus, are quoted in °C. and have not been corrected.

EXAMPLE 1

2-Benzylselenobenzoic acid

To a stirred suspension of 50.0 g (0.125 mol) diselenosalicylic acid in 380 ml water is added 38.0 g (0.95 mol) sodium hydroxide, when the internal temperature rises to 45° C. and the acid goes into solution. On addition of 100 g (0.94 mol) sodium carbonate and 58 g (0.33 mol) sodium dithionite the temperature increases to 55° C. The mixture is heated to reflux for 2 h, allowed to cool to room temperature and 47.6 ml (68.4 g; 0.4 mol) benzyl bromide is added dropwise within 10 minutes. Further water (100 ml) is added and the stirring is continued at room temperature for 14 hours, then 355 ml (32%) hydrochloric acid is slowly added to the reaction mixture with stirring, the precipitated white solid is filtered off and then washed to neutrality with water. The moist product is recrystallized from 1600 ml propanol with the addition of 3 g active charcoal. The yield is 48.8 g (67% of th.). The mother liquors yield a further 12 g (16.5%) 2-benzylselenobenzoic acid.

Yield 60.8 g (83.5% of th.)
mp 209°–210° C.

EXAMPLE 2

2-(4-Methylbenzylseleno)benzoic acid

To a suspension of 20.1 g (0.05 mol) diselenosalicylic acid in 20 ml water is added 15.0 g (0.375 mol) sodium hydroxide in one portion with stirring. After dissolution 39.75 g (0.375 mol) sodium carbonate and 23.9 g (0.1375 mol) sodium dithionite are added and the mixture is heated to reflux for 2 h, allowed to cool to room temperature and 30.1 g (0.1625 mol) 4-methylbenzyl bromide in 125 ml ethanol is added dropwise within 15 minutes, followed by stirring overnight. The reaction mixture is acidified under stirring with 150 ml aqueous hydrochloric acid (32%), the white precipitate is filtered off, washed with 200 ml water and dried. The residue is purified by recrystallization from ethyl acetate.
Yield 22 g (71% of th.)
mp 220°–222° C.

EXAMPLE 3

2-(4-Methoxybenzylseleno)benzoic acid

Repeating the procedure in example 2 but using 25.4 g (0.1625 mol) 4-methoxybenzyl chloride yields as reaction product 2-(4-methoxybenzylseleno)benzoic acid.
Yield 27.0 g (85% of th.)
mp 225°–228° C.

EXAMPLE 4

2-(4-Bromobenzylseleno)benzoic acid

Repeating the procedure in example 2 but using 40.6 g (0.1625 mol) 4-bromobenzyl bromide yields as reaction product 2-(4-bromobenzylseleno)benzoic acid.
Yield 31.4 g (84.7% of th.)
mp 255°–258° C.

EXAMPLE 5

2-(4-Cyanobenzylseleno)benzoic acid

Repeating the procedure in example 2 but using:
10 g (0.052 mol) 4-(cyanomethyl)benzonitrile in 100 ml ethanol,
6.3 g (0.016 mol) diselenosalicylic acid,
4.8 g (0.12 mol) sodium hydroxide,
12.7 g (0.12 mol) sodium carbonate,
7.7 g (0.044 mol) sodium dithionite and
100 ml distilled water.
Yield 7.4 g (73% of th.)
mp 252°–254° C.

EXAMPLE 6

2-(4-Nitrobenzylseleno)benzoic acid

Repeating the procedure in example 2 but using:
22.3 g (0.13 mol) 4-nitrobenzyl chloride in 250 ml ethanol,
16 g (0.04 mol) diselenosalicyclic acid,
12 g (0.3 mol) sodium hydroxide,
32 g (0.3 mol) sodium carbonate,
18.4 g (0.11 mol) sodium dithionite and
300 ml distilled water.
Yield 13.7 g (72% of th.)
mp 232°–235° C.

EXAMPLE 7

2-(4-Fluorobenzylseleno)benzoic acid

Repeating the procedure in example 2 but using:
23.5 g (19.5 ml; 0.16 mol) 4-fluorobenzyl chloride,
20 g (0.05 mol) diselenosalicyclic acid,
15 g (0.38 mol) sodium hydroxide,
40 g (0.39 mol) sodium carbonate,
24 g (0.14 mol) sodium dithionite and
400 ml distilled water.
Yield 22 g (71% of th.)
mp 220°–222° C.

EXAMPLE 8

2-(3-Chlorobenzylseleno)benzoic acid

Repeating the procedure in example 2 but using:
12 g (0.07 mol) 3-chlorobenzyl chloride (undiluted)
8 g (0.02 mol) diselenosalicylic acid,
6 g (0.15 mol) sodium hydroxide,
16 g (0.15 mol) sodium carbonate,
9.2 g (0.05 mol) sodium dithionite and
150 ml distilled water.
Yield 7.9 g (61% of th.)
mp 209°–211° C.

EXAMPLE 9

2-(4-Chlorobenzylseleno)benzoic acid

Repeating the procedure in example 2 but using:
20.9 g (0.13 mol) 4-chlorobenzyl chloride in 100 ml ethanol,
16 g (0.04 mol) diselenosalicylic acid,
12 g (0.3 mol) sodium hydroxide,
32 g (0.3 mol) sodium carbonate,
18.4 g (0.11 mol) sodium dithionite and
150 ml distilled water.
Yield 21 g (80.6% of th.)
mp 234°–237° C.

EXAMPLE 10

2-Benzylseleno-3-methoxybenzoic acid

A suspension of 13.5 g (0.0362 mol) 4,4-dimethyl-2-(2-benzylseleno-3-methoxyphenyl)-1,3-oxazoline in 21.5 ml (0.181 mol) benzyl bromide is stirred at room temperature for 24 hours and the solvent removed. The residue is dissolved in a mixture of 1.8 l caustic soda solution (20%) and 1.8 l methanol and heated under reflux for 24 hours, the contents of the flask are extracted with 300 ml diethyl ether and the organic phase so obtained discarded. The aqueous phase is adjusted to pH 1 with concentrated hydrochloric acid, the precipitated solid filtered off, washed with 200 ml water and dried.
Yield 6.9 g (59.6% of th.)
mp 151°–153° C.

EXAMPLE 11

2-Benzylseleno-3,4-methylenedioxybenzoic acid

Repeating the procedure in example 10 but using:
2.45 g (0.0063 mol) 4,4-dimethyl-2-(2-benzylseleno-3,4-methylenedioxyphenyl)-1,3-oxazoline in
5.4 g (0.032 mol) benzyl bromide
Yield 1.6 g (75.8% of th.)
mp 196°–197° C.

EXAMPLE 12

2-Benzylseleno-3-fluorobenzoic acid

Repeating the procedure in example 10 but using:
43.5 g (0.12 mol) 4,4-dimethyl-2-(2-benzylseleno-3-fluorophenyl)-1,3-oxazoline in
102.6 g (0.6 mol) benzyl bromide In this case the residue of the ethereal phase after extraction was not discarded, but redissolved in benzyl bromide and treated as in example 10. After adjustment of the aqueous phase to pH 1 it was washed first with water and then, after drying, with n-hexane.

Total yield 29.9 g (80.6% of th.)
mp 137°–138° C.

EXAMPLE 13

4,4-Dimethyl-2-(2-benzylseleno-3-fluorophenyl)-1,3-oxazoline

To a solution of 30.0 g 4,4-dimethyl-2-(3-fluorophenyl)-1,3-oxazoline in 400 ml anhydrous tetrahydrofuran that has been cooled to −45° C. is added dropwise with stirring 100 ml of a 1.6M solution of n-butyllithium in hexane at such a rate that the temperature does not rise above −40° C. (25 minutes). After stirring for two hours at −45° C. the reaction mixture is warmed to 0° C. and treated dropwise within 20 minutes with a solution of 54.7 g (0.16 mol) dibenzyl diselenide in 250 ml anhydrous tetrahydrofuran. The reaction mixture is then stirred for 18 hours at room temperature. The contents of the flask are taken up in 300 g ice and 300 ml water and extracted twice with 300 ml portions of diethyl ether. The organic phase is extracted successively with 200 ml water, 200 ml 10% sodium hydrogen carbonate solution and 200 ml water, dried over sodium sulfate and the solvent removed in vacuum. The crude product (58.3 g) is purified by column chromatography (silica gel/dichloromethane).

Yield 43.5 g (75% of th.)
mp 95° C.

EXAMPLE 14

4,4-Dimethyl-2-(2-benzylseleno-3-methoxyphenyl)-1,3-oxazoline

Repeating the procedure in example 13 but using:
50 g (0.244 mol) 4,4-dimethyl-2-(3-methoxyphenyl)-1,3-oxazoline in 500 ml anhydrous tetrahydrofuran
167.5 ml (0.268 mol) 1.6M solution of n-butyllithium in hexane
91 g (0.268 mol) dibenzyl diselenide
Yield 28 g (30.7% of th.)
TLC (SiO$_2$): R$_f$ 0.23 (CH$_2$Cl$_2$)

EXAMPLE 15

4,4-Dimethyl-2-(2-benzylseleno-3,4-methylenedioxyphenyl)-1,3-oxazoline

To a solution of 4.4 g (0.02 mol) 4,4-dimethyl-2-(3,4-methylenedioxyphenyl)-1,3-oxazoline in 100 ml tetrahydrofuran (anhydrous) which has been cooled to 0° C. is added dropwise with stirring within 1 h 25 ml of a 1.6M n-butyllithium solution in hexane. After 30 h at 0° C. a solution of 6.2 g (0.02 mol) dibenzyl diselenide in 100 ml tetrahydrofuran (anhydrous) is added dropwise with stirring. The mixture is stirred for 2 hours at 0° C. and then treated with 20 ml water, the solvent is then removed under vacuum from the contents of the flask and the residue taken up in 100 ml dichloromethane and 100 ml water. The organic phase is separated and the solvent removed under vacuum. The crude product is purified by column chromatography (silica gel/dichloromethane).

Yield 2.45 g (31.6% of th.)
mp 107°–109° C.

EXAMPLE 16

N-(4-Methylphenyl)-2-benzylselenobenzamide

A suspension of 4 g (0.013 mol) 2-benzylselenobenzoic acid in 80 ml dichloromethane is cooled to 0°–5° C. and treated with stirring with 2 g (0.015 mol) chloromethylenedimethyliminium chloride (Vilsmeir's reagent) in one portion. After 1 hour a solution of 1.47 g (0.0137 mol) 4-methylaniline and 3 g (0.03 mol) triethylamine are added dropwise in the cold and stirring continued for 2 hours at room temperature. The solution is washed successively with 100 ml 1N aqueous hydrochloric acid
100 ml 1N sodium hydroxide solution and
100 ml distilled water, dried over Na$_2$SO$_4$ and the solvents removed under vacuum. The residue is recrystallized from 2-propanol.

Yield 2.56 g (49% of th.)
mp 165°–166° C.

EXAMPLE 17

N-(4-Methoxyphenyl)-2-benzylselenobenzamide

Repeating the procedure in example 16 the product N-(4-methoxyphenyl)-2-benzylselenobenzamide is obtained by using 1.69 g (0.0137 mol) 4-methoxyaniline in place of 4-methylaniline.

Yield 3.73 g (69.1% of th.)
mp 182°–183° C.

EXAMPLE 18

N-(4-Fluorophenyl)-2-benzylselenobenzamide

Repeating the procedure in example 16 the product N-(4-fluorophenyl)-2-benzylselenobenzamide is obtained by using 1.52 g (0.0137 mol) 4-fluoroaniline.

Yield 2.50 g (47.4% of th.)
mp 129°–131° C.

EXAMPLE 19

N-[4-(N',N'-Dimethylamino)phenyl]-2-benzylselenobenzamide

Repeating the procedure in example 16 but using 1.87 g (0.0137 mol) 4-N,N-dimethylaminoaniline yields a dichloromethane solution that is washed three times with 100 ml portions of distilled water, dried with sodium sulfate and the solvent removed in vacuum. The crude product is purified by recrystallization from 2-propanol.

Yield 1.77 g (31.7% of th.)
mp 163°–165° C.

EXAMPLE 20

N-(4-Hydroxyphenyl)-2-benzylselenobenzamide

Repeating the procedure in example 16 but using 1.5 g (0.0137 mol) 4-aminophenol yields a dichloromethane solution that is washed with 200 ml 1N hydrochloric acid and two 200 ml portions of distilled water, dried with sodium sulfate and the solvent removed in vacuum. The residue is purified by column chromatography (silica gel/dichloromethane).

Yield 1.31 g (25% of th.)

mp 139°-140° C.

EXAMPLE 21

2-Benzylselenobenzanilide

A suspension of 6 g (0.0206 mol) 2-benzylselenobenzoic acid in 60 ml dichloromethane is treated at −10° C. with 2.64 g (0.0206 mol) chloromethylenedimethyliminium chloride (Vilsmeier's reagent). After stirring for 30 minutes at 0° C. the clear reaction mixture is treated dropwise within 15 min with a solution of 1.9 g (0.04 mol) aniline and 4.21 g (0.0416 mol) triethylamine in 60 ml dichloromethane. After stirring for 48 h at room temperature the clear yellow solution is extracted with 1N HCl (100 ml) followed by water until it is neutral, the organic phase is dried over $Na_2SO_4$ and then evaporated to dryness in vacuum. The solid crude product is recrystallized from 2-propanol (220 ml).

Yield 5.5 g (72.9% of th.)
mp 132°-133° C.

EXAMPLE 22

N-(4-Chlorophenyl)-2-benzylselenobenzamide

To a solution of 6 g (0.0206 mol) 2-benzylselenobenzoic acid and 2.1 g (0.0206 mol) triethylamine in 100 ml dichloromethane at 0°-5° C. is added in one portion 5.24 g (0.0206 mol) bis[2-oxo-3-oxazolidinyl]phosphoryl chloride. After stirring for 30 minutes a solution of 2.63 g (0.0206 mol) 4-chloroaniline at 0° C. is added and after 15 minutes a solution of 2.1 g (0.0206 mol) triethylamine in 30 ml dichloromethane (within 2½ hours). The reaction mixture is then immediately extracted with 100 ml 1N aqueous hydrochloroic acid solution, 100 ml 1N caustic soda solution and 100 ml distilled water. The organic phase is dried with sodium sulfate and the solvent removed under vacuum. The residue is purified by recrystallization from 80 ml 2-propanol.

Yield 6.60 g (79.9% of th.)
mp 160°-161° C.

EXAMPLE 23

N-(4-Cyanophenyl)-2-benzylselenobenzamide

Repeating the procedure in example 22 but using 2.43 g (0.0206 mol) 4-aminobenzonitrile (instead of 4-chloroaniline) a crude product is obtained that is recrystallized once from 80 ml 2-propanol. The crystals so obtained are discarded. The mother liquor is treated with 80 ml n-hexane. The precipitate is filtered off and purified by column chromatography (silica gel/dichloromethane).

Yield 1.54 g (19.1% of th.)
mp 153°-154° C.

EXAMPLE 24

N-(4-Nitrophenyl)-2-benzylselenobenzamide

Repeating the procedure in example 23 but using 2.84 g (0.0206 mol) 4-nitroaniline yields N-(4-nitrophenyl)-2-benzylselenobenzamide.

Yield 1.33 g (15.7% of th.)
mp 195°-196° C.

EXAMPLE 25

N-Ethyl-N-(4-fluorophenyl)-2-benzylselenobenzamide

Repeating the procedure in example 22 but using:
3.0 g (0.0103 mol) 2-benzylselenobenzoic acid
1.44 ml triethylamine in 20 ml dichloromethane
2.26 g (0.0103 mol) bis[2-oxo-3-oxazolidinyl]phosphoryl chloride
1.43 g (0.0103 mol) N-ethyl-4-fluoroaniline and
1.44 ml triethylamine in 10 ml dichloromethane.

After the last addition, however, the reaction mixture is allowed to stand for 18 h at room temperature then extracted twice with 100 ml water. The dichloromethane phase is then treated as described in example 22 and the crude product is purified by column chromatography (silica gel/dichloromethane).

Yield 1.25 g (29.5% of th.)
mp 121°-122° C.

EXAMPLE 26

R(+)-N-(1-Phenylethyl)-2-benzylselenobenzamide

To a suspension of 7.28 g (0.025 mol) 2-benzylselenobenzoic acid in 100 ml dimethylformamide is added 4.45 g (0.0275 mol) N,N'-carbonyldiimidazole and the solution, which becomes clear after 5 minutes, is stirred until the evolution of $CO_2$ ceases. After addition of 3.03 g (0.025 mol) R(+)-1-phenylethylamine the mixture is heated under reflux for 1 h and then stirred at room temperature for a further 5 h. The solvent is removed in vacuum, the residue dissolved in 100 ml dichloromethane and this solution extracted successively with 100 ml 1N hydrochloric acid, 100 ml 1N sodium hydroxide and 100 ml water. The organic phase is dried over $Na_2SO_4$, filtered and the solvent removed in vacuum. The residue (10 g solid product) which is inhomogeneous on TLC ($CH_2Cl_2$:MeOH=9:1) is purified by flash chromatography, the eluate which is uniform on TLC is concentrated to dryness and recrystallized from toluene. The eluent employed for flash chromatography is dichloromethane and the stationary phase flash silica gel.

Yield 5.7 g (57.8% of th.)
mp 105°-107° C.
$[\alpha]_D^{20}$ +67.5° (c=1, EtOH)

EXAMPLE 27

S(−)-N-(1-Phenylethyl)-2-benzylselenobenzamide

Repeating the procedure in example 26 the optical antipode is obtained by using 3.03 g (0.025 mol) S(−)-1-phenylethylamine.

Yield 4.9 g (49.7% of th.)
mp 105°-107° C.
$[\alpha]_D^{20}$ −68.6° (c=1, EtOH)

EXAMPLE 28

N-Phenyl-2-(4-methylbenzylseleno)benzamide

To a solution of 1.58 g (0.00517 mol) 2-(4-methylbenzylseleno)benzoic acid (example 2) and 0.58 g (0.00573 mol) triethylamine in 10 ml dichloromethane which has been cooled to 0° C. is added 1.32 g (0.00517 mol) solid bis[2-oxo-3-oxazolidinyl]phosphoryl chloride in one portion. After stirring for 30 minutes a solution of 0.48 g aniline (0.47 ml; 0.00517 mol) in 10 ml dichloromethane and 0.74 g (1.02 ml; 0.00573 mol) triethylamine in 10 ml dichloromethane is added dropwise with stirring. The reaction mixture is stirred for 20 hours at room temperature and treated with 20 ml distilled water. The organic phase is separated and extracted successively with 20 ml water, two 25 ml portions of 10% hydrochloric acid and two 25 ml portions of 10% sodium hydroxide solution and dried. The solvent is then removed and the residue purified by column chromatography (silica gel/dichloromethane).
Yield 1.9 g (96% of th.)
mp 140° C.

EXAMPLE 29

N-Phenyl-2-(4-methoxybenzylseleno)benzamide

Repeating the procedure in example 28 but using 1.66 g (0.00517 mol) 2-(4-methoxybenzylseleno)benzoic acid (example 3) yields N-phenyl-2-(4-methoxybenzylseleno)benzamide as product.
Yield 1.8 g (88% of th.)
mp 132°–133° C.

EXAMPLE 30

N-Phenyl-2-(4-bromobenzylseleno)benzamide

Repeating the procedure in example 28 but using 1.92 g (0.00517 mol) 2-(4-bromobenzylseleno)benzoic acid (example 4) yields N-phenyl-2-(4-bromobenzylseleno)benzamide as product.
Yield 2 g (87% of th.)
mp 155° C.

EXAMPLE 31

N-Phenyl-2-(4-cyanobenzylseleno)benzamide

Repeating the procedure in example 28 but using 1.63 g (0.00517 mol) 2-(4-cyanobenzylseleno)benzoic acid (example 5) yields N-phenyl-2-(4-cyanobenzylseleno)benzamide as product.
Yield 1.78 g (88% of th.)
mp 148°–149° C.

EXAMPLE 32

N-Phenyl-2-(4-nitrobenzylseleno)benzamide

Repeating the procedure in example 28 but using 1.74 g (0.00517 mol) 2-(nitrobenzylseleno)benzoic acid (example 6) yields N-phenyl-2-(4-nitrobenzylseleno)benzamide as product.
Yield 1.8 g (84.7% of th.)
mp 107°–108° C.

EXAMPLE 33

N-Phenyl-2-(4-fluorobenzylseleno)benzamide

Repeating the procedure in example 28 but using 1.6 g (0.00517 mol) 2-(4-fluorobenzylseleno)benzoic acid (example 7) yields N-phenyl-2-(4-fluorobenzylseleno)benzamide as product.
Yield 1.44 g (72.5% of th.)
mp 131°–132° C.

EXAMPLE 34

N-Phenyl-2-(4-chlorobenzylseleno)benzamide

Repeating the procedure in example 28 but using 1.68 g (0.00517 mol) 2-(4-chlorobenzylseleno)benzoic acid (example 9) yields N-phenyl-2-(4-chlorobenzylseleno)benzamide as product.
Yield 1.68 g (81.1% of th.)
mp 151°–152° C.

EXAMPLE 35

N-Ethyl-N-(4-fluorophenyl)-2-benzylseleno-3-fluorobenzamide

To a stirred solution of 0.47 g (0.0036 mol) N-ethyl-4-fluoroaniline in 10 ml pyridine which has been cooled to 0° C. is added dropwise a solution of 1.1 g (0.0036 mol) 2-benzylseleno-3-fluorobenzoyl chloride. This was previously prepared from 2-benzylseleno-3-fluorobenzoic acid (example 12) and α,α-dichloromethyl methyl ether in dichloromethane at room temperature.

After stirring for 4 hours at room temperature the contents of the flask are poured onto 200 g ice and 100 ml water, extracted three times with 100 ml portions of dichloromethane and the combined dichloromethane phases are evaporated to dryness in vacuum after being dried over Na$_2$SO$_4$ and filtered. The solid residue (1.5 g) is treated with 100 ml hexane, filtered off and dried, yielding 1.05 g solid substance. Since it is not homogeneous on TLC the solid substance is dissolved once again in 150 ml dichloromethane and shaken with two 50 ml portions of 10% sodium carbonate solution, the organic phase dried over Na$_2$SO$_4$ and the solvent removed; the new solid residue is recrystallized from 50 ml hexane/dichloromethane (1:1).
Yield 0.85 g (58.8%)
mp 88°–89° C.

EXAMPLE 36

N-Benzyl-2-benzylseleno-3-fluorobenzamide

Repeating the procedure in example 35 the named compound is obtained by the reaction of
1.27 g (0.00388 mol) 2-benzylseleno-3-fluorobenzoyl chloride and
0.42 g (0.00388 mol) benzylamine in 50 ml pyridine.
Yield 0.82 g (53.1% of th.)
mp 128°–129° C.

EXAMPLE 37

N-methyl-N-phenyl-2-benzylseleno-3-methoxybenzamide

Repeating the procedure in example 28 but using 2 g (0.0062 mol) 2-benzylseleno-3-methoxybenzoic acid (example 10) yields N-methyl-N-phenyl-2-benzylseleno-3-methoxybenzamide as product.
Yield 1.25 g (50% of th.)
mp 111° C.

EXAMPLE 38

2-Benzylseleno-3-fluorobenzanilide

Repeating the procedure in example 28 but using 1.6 g (0.0052 mol) 2-benzylseleno-3-fluorobenzoic acid (example 12) yields 2-benzylseleno-3-fluoroanilide as product.
Yield 1.5 g (78% of th.)
mp 138° C.

EXAMPLE 39

2-Benzylseleno-3-methoxybenzanilide

To a solution of 1.37 g (0.0041 mol) 2-benzylseleno-3-methoxybenzoyl chloride (prepared from 2-benzylseleno-3-methoxybenzoic acid and α,α-dichloromethyl ether in dichloromethane at room temperature) in 10 ml pyridine at 0° C. is added with stirring a solution of 0.38 g (0.0041 mol−0.37 ml) aniline. After stirring at room temperature for 18 hours the contents of the flask are poured onto 150 g ice and 50 ml 25% HCl and extracted. The organic phase is washed with 50 ml 10% NaHCO$_3$ and twice with 100 ml portions of dichloromethane and 200 ml water, dried over sodium sulfate and the solvent removed in vacuum.

The residue is cleaned up by column chromatography (silica gel/dichloromethane). An oil is obtained IR (KBr) 1667 (m), 755 cm$^{-1}$ (S).

Yield 1.1 g (68.5% of th.)

EXAMPLE 40

2-Benzylseleno-3,4-methylenedioxybenzanilide

To a solution of 1.6 g (0.0048 mol) 2-benzylseleno-3,4-methylenedioxybenzoic acid and 0.48 g triethylamine in 50 ml dichloromethane at 0° C. is added in one portion 1.22 g (0.0048 mol) solid bis[2-oxo-3-oxazolidinyl]phosphoryl chloride. After stirring for 30 min 0.44 g (0.44 ml) aniline in 5 ml dichloromethane are added at 0° C. dropwise with stirring followed after 1 hour by a solution of 0.48 g (0.66 ml) triethylamine in 10 ml dichloromethane. After 90 minutes at room temperature the reaction mixture is extracted successively with 50 ml 1N HCl and 50 ml water. The organic phase is dried over sodium sulfate and the solvent removed in vacuum. The crude product is purified by recrystallization from 2-propanol.

Yield 0.7 g (35.9% of th.)

mp 141°–142° C.

EXAMPLE 41

N-Phenyl-2-(3-chlorobenzylseleno)benzamide

Repeating the procedure in example 17 but using 1.68 g (0.00517 mol) 2-(3-chlorobenzylseleno)benzoic acid (example 8) yields N-phenyl-2-(3-chlorobenzylseleno)-benzamide as product.

Yield 1.6 g (77.2% of th.)

mp 131°–132° C.

We claim:

1. A compound of the Formula (I)

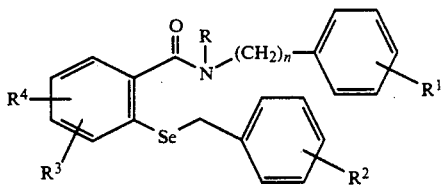

where

R is hydrogen, methyl or ethyl and $R^1$ is hydrogen, fluorine, chlorine, bromine, $C_{1-4}$-alkyl, $C_{1-4}$-alkoxy, hydroxy, cyano, nitro, or dimethylamino;

$R^2$ is hydrogen, fluorine, chlorine, bromine, $C_{1-4}$-alkyl, $C_{1-4}$-alkoxy, cyano, or nitro;

$R^3$ and $R^4$ are independent hydrogen, fluorine, or $C_{1-4}$-alkoxy, or together form methylenedioxy; and n is zero, 1 or 2.

2. The compound of the Formula (I) defined in claim 1 and selected from the group consisting of:

N-ethyl-N-(4-fluorophenyl)-2-benzylselenobenzamide;

N-benzyl-2-benzylseleno-3-fluorobenzamide; and

N-methyl-N-phenyl-2-benzylseleno-3-methoxybenzamide.

3. N-benzyl-2-benzylseleno-3-fluorobenzamide as defined in claim 1.

4. An anti-inflammatory pharmaceutical composition which comprises as active ingredient, an anti-inflammatorily effective amount of the compound of the Formula (I) defined in claim 1 in admixture with a pharmaceutically acceptable inert carrier.

5. An anti-inflammatory method of treatment which comprises administering to a subject susceptible to inflammation, an anti-inflammatorily effective amount of the compound of the Formula (I) defined in claim 1.

* * * * *